United States Patent
Birnkrant et al.

(10) Patent No.: US 10,339,778 B1
(45) Date of Patent: Jul. 2, 2019

(54) CHAMBERLESS AIR QUALITY MONITORS WITH TEMPERATURE SENSING

(71) Applicant: Kidde Technologies, Inc., Wilson, NC (US)

(72) Inventors: Michael J. Birnkrant, Wethersfield, CT (US); David L. Lincoln, Johnston, RI (US)

(73) Assignee: Kidde Technologies, Inc., Wilson, NC (US)

( * ) Notice: Subject to any disclaimer, the term of this patent is extended or adjusted under 35 U.S.C. 154(b) by 0 days.

(21) Appl. No.: 15/871,633

(22) Filed: Jan. 15, 2018

(51) Int. Cl.
    *G08B 17/10* (2006.01)
    *G08B 17/107* (2006.01)

(52) U.S. Cl.
    CPC .................... *G08B 17/107* (2013.01)

(58) Field of Classification Search
    CPC ................ G08B 17/107; G08B 29/145; Y10T 436/205831
    USPC .......................... 340/630, 628, 629, 632, 634
    See application file for complete search history.

(56) References Cited

U.S. PATENT DOCUMENTS

| | | | |
|---|---|---|---|
| 4,111,559 | A | 9/1978 | Smith et al. |
| 6,208,252 | B1 | 3/2001 | Danilychev |
| 9,652,958 | B2 | 5/2017 | Zribi et al. |
| 9,659,485 | B2 | 5/2017 | Piccolo, III |
| 2002/0153499 | A1 | 10/2002 | Oppelt et al. |
| 2009/0218526 | A1 | 9/2009 | Shaw et al. |
| 2011/0216317 | A1* | 9/2011 | Marra .................. G01N 1/2202 356/335 |
| 2012/0161796 | A1* | 6/2012 | Smith .................. G01N 27/125 324/693 |
| 2013/0174646 | A1* | 7/2013 | Martin .................. G01N 33/00 73/31.02 |

(Continued)

FOREIGN PATENT DOCUMENTS

| EP | 3029648 A1 | 6/2016 |
|---|---|---|
| WO | 2017218763 A1 | 12/2017 |

OTHER PUBLICATIONS

Extended European search report for European Patent Application No. 18176075.2 dated Jul. 30, 2018.

(Continued)

*Primary Examiner* — Toan N Pham
(74) *Attorney, Agent, or Firm* — Locke Lord LLP; Scott D. Wofsy; Alicia J. Carroll

(57) ABSTRACT

A chamberless indoor air quality monitor system includes a detector body. A resistive heater is operatively connected to the detector body. An active temperature sensor operatively connected to the resistive heater and operatively connected to an outer surface of the detector body configured to take an active temperature measurement. A method for measuring temperature in a chamberless indoor air quality monitor system includes generating an active temperature measurement with an active temperature sensor operatively connected to an outer surface of the detector body. The method includes heating the active temperature sensor with a resistive heater operatively connected to the detector body. The method includes comparing the active temperature measurements to one another to generate a corrected active temperature measurement based on a temperature difference over time between one or more of the active temperature measurements.

21 Claims, 3 Drawing Sheets

(56) References Cited

U.S. PATENT DOCUMENTS

| | | | | |
|---|---|---|---|---|
| 2016/0097748 A1* | 4/2016 | Hansen | ................ | G01N 30/06 |
| | | | | 73/23.37 |
| 2017/0206764 A1 | 7/2017 | Zribi et al. | | |
| 2017/0248699 A1 | 8/2017 | Fang et al. | | |
| 2017/0310809 A1* | 10/2017 | Shi | ................... | H04M 1/72527 |
| 2018/0156747 A1* | 6/2018 | Le Neel | ............ | G01N 33/0047 |

OTHER PUBLICATIONS

Extended European search report for European Patent Application No. 18176082.8 dated Jul. 31, 2018.

\* cited by examiner

CHAMBERLESS AIR QUALITY MONITORS WITH TEMPERATURE SENSING

BACKGROUND OF THE INVENTION

1. Field of the Invention

The present disclosure relates to smoke detectors, and more particularly to chamberless smoke detectors, air quality detection and temperature monitoring for aircraft.

2. Description of Related Art

Smoke sensors and air quality monitors, or combinations thereof, such as those used on aircraft, are often located inside of a cabin, bathroom or cargo area, use near infrared light, or lights of other wavelengths, scattering inside a small plastic chamber located inside of the enclosure, with inlets of controlled dimensions to prevent entry of unwanted particles. These detectors can sometimes include temperature sensors to detect the temperature within the chamber. Over time, these undesired particles may also collect at the inlets of the sensor chamber, making it more difficult for smoke particles to diffuse into the chamber. Additionally, particles collecting on chamber surfaces may increase sensitivity thereby resulting in more frequent false or nuisance alarms. Moreover, the enclosure of some detectors can be covered over, thereby inhibiting the detection capabilities.

To alleviate some of these issues, chamberless smoke detectors may be used. However, with no chamber there is not a physically well-protected measurement volume, meaning a well-defined operational strategy is key to maintaining measurement integrity. Further, it is often desired to monitor temperature with the chamberless smoke detectors. However, temperature sensors exposed to an open environment, as opposed to a closed volume in a chamber-style detector, may have an increased susceptibility to false alarms.

The conventional techniques have been considered satisfactory for their intended purpose. However, there is an ever present need for improved chamberless temperature monitoring.

SUMMARY OF THE INVENTION

A chamberless indoor air quality monitor system includes a detector body. A resistive heater is operatively connected to the detector body. An active temperature sensor operatively connected to the resistive heater and operatively connected to an outer surface of the detector body configured to take an active temperature measurement.

A printed circuit board (PCB) can be disposed at the detector body. A processor can be operatively connected to the PCB and/or the active temperature sensor. The processor can be configured to receive active temperature measurements from the active temperature sensor and generate a corrected active temperature measurement based on a temperature difference over time between one or more active temperature measurements. The system can include a passive temperature sensor operatively connected to the PCB and enclosed within the detector body configured to take a passive temperature measurement. In some embodiments, the passive and/or active temperatures sensors are resistance-temperature detectors (RTD), and/or thermocouples.

In accordance with some embodiments, the system includes one or more light sources operatively connected to the detector body configured to emit light into a monitored space. The system can include at least three light sensing devices operatively connected to the detector body configured to receive scattered light emitted from the one or more light sources. The at least three light sensing devices can share a common centerline axis configured to provide overlapping sensing regions for close proximity detection of the scattered light. The processor can be configured to evaluate the received scattered light signals for presence of one or more indoor air quality conditions in the monitored space.

In accordance with another aspect, a method for measuring temperature in a chamberless indoor air quality monitor system includes generating an active temperature measurement with an active temperature sensor operatively connected to an outer surface of the detector body. The method includes heating the active temperature sensor with a resistive heater operatively connected to the detector body. The method includes comparing the active temperature measurements to one another to generate a corrected active temperature measurement based on a temperature difference over time between one or more of the active temperature measurements.

The method can include generating a passive temperature measurement with a passive temperature sensor operatively connected to a printed circuit board (PCB) and enclosed within a detector body. Generating the corrected active temperature measurement based on the temperature difference over time between one or more of the active temperature measurements can include comparing the active temperature measurements before and after heating with the resistive heater. The method can include determining an air velocity across the active temperature sensor. Determining the air velocity across the active temperature sensor includes stopping heat to the active temperature sensor and using the rate of decay of the active temperature measurements to determine the air velocity. The method can include automatically adjusting the generated corrected active temperature measurement to account for changes in thermal mass of the chamberless indoor air quality monitor system due to a build-up of debris that may become deposited over time on the chamberless indoor air quality monitor system In accordance with another aspect, an aircraft management system includes chamberless indoor air quality monitor systems, similar to the chamberless indoor air quality monitor system described above. An aircraft management computer is operatively connected to each of the chamberless indoor air quality monitor systems to correlate and compare data across each of the chamberless indoor air quality monitor systems.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
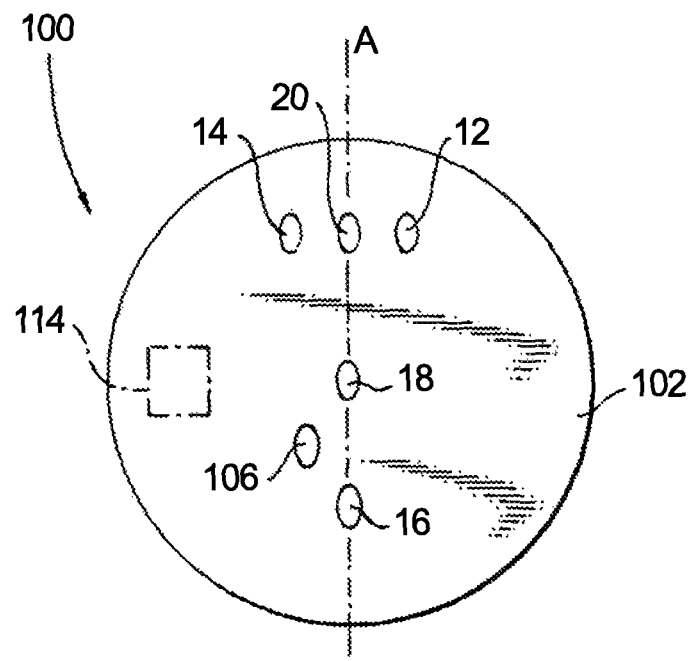
FIG. 1 is a schematic diagram of an exemplary embodiment of a chamberless indoor air quality monitor system constructed in accordance with the present disclosure, showing an active temperature sensor on the outer surface of the detector body.

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 100. Other embodiments of systems in accordance with the disclosure, or aspects thereof, are provided in FIGS. 2-6, as will be described. The systems and methods described herein can be used for sensing temperature or air velocity near a chamberless indoor air quality monitor while being more robust to nuisances in the monitored environment, and for providing more accurate temperature measurements. Moreover, a chamberless detector design can be flush mounted for minimal intrusion into the monitored environment, reduced weight and simplified maintenance.

As shown in FIG. 1, a chamberless indoor air quality monitor system 100 includes a detector body 102, a plurality of light sources and a plurality of light sensing devices. In an embodiment, the plurality of light sources includes a first light source 12 and a second light source 14. The first light source 12 and the second light source 14 may include a light emitting diode (LED). The first light source 12 and the second light source 14 may emit light at one or more wavelengths into monitored space 107, which may be an airplane cabin, bathroom, cargo area or the like, into which the light is emitted. In accordance with one embodiment, the first light source 12 is configured to emit light of wavelengths characteristic of infrared light, and the second light source 14 is configured to emit light of wavelengths characteristic of blue visible light. The infrared light may be used in the detection and false alarm discrimination of smoke, and the blue visible light may be used in the false alarm discrimination of smoke.

With continued reference now to FIG. 1, the plurality of light sensing devices includes a first light sensing device 16, a second light sensing device 18, and a third light sensing device 20 located within different regions of the smoke detector 10 with a line of sight of the light emitted from the first light source 12 and the second light source 14. The overlap of the field of view of the first light sensing device 16, second light sensing device 18, and third light sensing device 20 with the emissions of the first light source 12 and the second light source 14 form different overlapping sensing volumes. The light sensing devices are configured to measure signals from the first light source 12 and the second light source 14. In some embodiments, the three light sensing devices 16, 18 and 20 share a common centerline axis A configured to provide overlapping sensing regions for close proximity detection of the scattered light. In some embodiments, light sensing devices, 16, 18 and 20 are photodiodes. The light sensing devices are not limited to photodiodes and could include light sensing devices such as Avalanche PhotoDiodes (APDs), Multi-Pixel Photon Counters (MPPCs), and other photodetectors. The system includes a processor 114 configured to evaluate the received scattered light signals for presence of one or more indoor air quality conditions in the monitored space.

Figure 2:
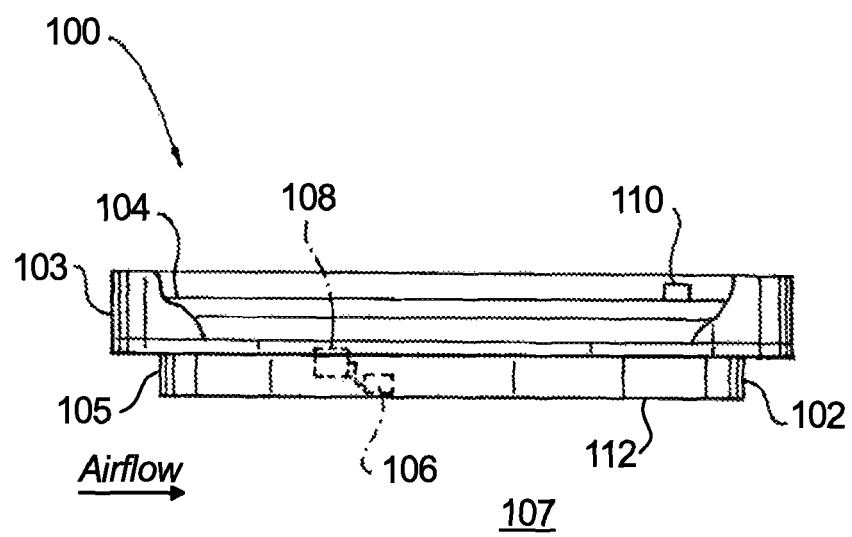
FIG. 2 is a schematic side view of the chamberless indoor air quality monitor system of FIG. 1, showing the resistive heater operatively connected to the active temperature sensor.

With continued reference now to FIGS. 1-2, the detector body 102 includes an upper housing portion 103 and a lower faceplate portion 105. The chamberless indoor air quality monitor system 100 includes an active temperature sensor 106 mounted in the lower faceplate portion 105 of the detector body 102 that is exposed to the monitored space 107. A printed circuit board (PCB) 104 is disposed within the upper housing portion 103 of the detector body 102. A passive temperature sensor 110 is operatively connected to the PCB 104 and enclosed within the upper housing portion 103 of the detector body 102 configured to take a passive temperature measurement of the interior of detector body 102. Passive temperature sensor 110 may fluctuate based on heat emitted from various electrical components in the detector body 102.

With continued reference to FIG. 2, the active temperature sensor 106 is operatively connected to the PCB 104 and operatively connected to a bottom surface 112 of the lower faceplate portion 105 of the detector body 102, exposed to the monitored space 107, and configured to take active temperature measurements. Bottom surface 112 is the bottom surface of detector body 102 and faceplate portion 105. Passive temperature sensor 110 is mounted on PCB 104 to face away from the monitored space 107. Depending on the type of detector, or other parameter, the passive and active temperatures sensors can be resistance-temperature detectors (RTD) and/or thermocouples. The processor 114 is operatively connected to the PCB 104 configured to receive and compare multiple temperatures from the active temperature sensor 106 and also a temperature measurement from the passive temperature sensor 110, as described above.

With reference now to FIG. 2, a resistive heater 108 is operatively connected to the detector body 102 and active temperature sensor 106. Resistive heater 108 is mounted within the lower faceplate portion 105 proximate to active temperature sensor 106 and proximate to the bottom surface 112 of the lower faceplate portion 105. Active temperature sensor 106 is exposed to the monitored space 107. The resistive heater 108 is in thermal contact with active temperature sensor 106 to heat active temperature sensor 106. In an embodiment, for example, resistive heater 108 is on one side of a small PCB board (not shown) and active temperature sensor 106 is on the other side of the PCB board. The active temperature sensor 106 measures the temperature of the monitored space 107. However, the accuracy of the temperature measurement can be degraded due to dust and water vapor covering the temperature sensor. The unwanted buildup of material thermally insulates the active temperature sensor 106 from the environment. The buildup of material also increases the thermal mass between the resistive heater 108 and active temperature sensor 106.

Figure 5:
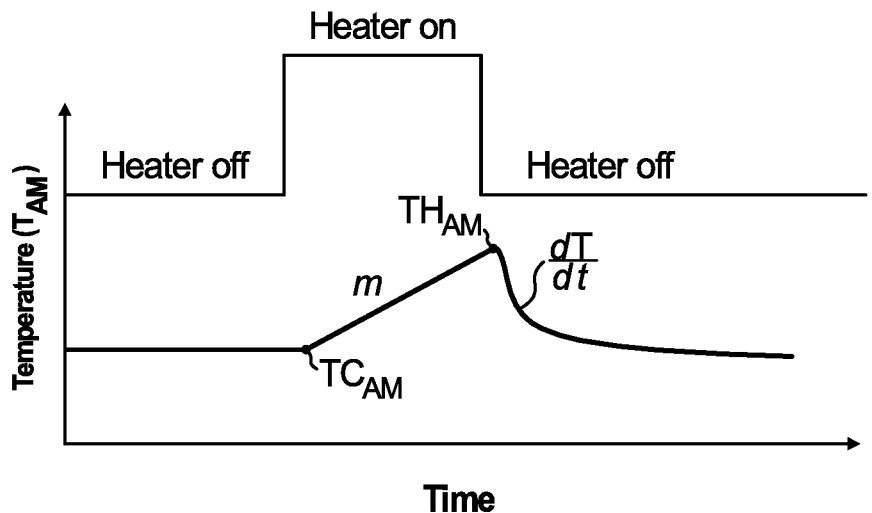
FIG. 5 illustrates a chart schematically showing the relationship between the change in the measured active temperatures and the heating applied by the resistive heater.

With reference now to FIGS. 2 and 5, resistive heater 108 periodically receives electrical pulses generating heat in its resistive element. Since resistive heater 108 and active temperature sensor 106 are in thermal contact with one another, the periodic heating from resistive heater 108 periodically increases the measured temperatures ($T_{AM}$) at active temperature sensor 106. The temperature difference ($\Delta T$) over time (e.g. the slope m), shown in FIG. 5, between when the resistive heater 108 is off and on is related to the detector thermal mass (which can change depending on build-up and debris that may be deposited on the detector). A calibration factor (f) associated with active temperature sensor 106 and the slope m are then used to determine the corrected temperature ($T_{CA}$) based on a measured temperature ($T_{AM}$) from active temperature sensor 106 at a given time ($T_{CA}=m \times T_{AM} \times f$). The calibration factor (f) is determined, in one aspect, by using the slope of temperature change m related to thermal mass between sensor and heater. This allows the corrected temperature ($T_{CA}$) to take into account changes due to build up of debris on detector, providing a more accurate temperature measurement for the monitored area 107.

Figure 6:
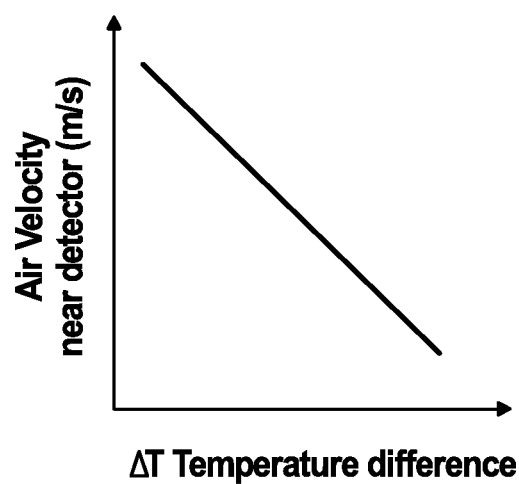
FIG. 6 illustrates a chart schematically showing the relationship between the difference between the measured active temperatures and airflow velocity.

As shown in FIGS. 2, 5 and 6, in some embodiments, the output from active temperature sensor 106 is used for monitoring the air flow near the sensor. Airflow velocity can be determined by using the change in temperature between a cold temperature when the heater 108 is off ($TC_{AM}$) and a max temperature when the heater 108 is on ($TH_{AM}$). The difference is then correlated to airflow velocity by multiplying the difference by a fixed parameter a, and is schematically indicated by the chart in FIG. 6. Airflow velocity can also be determined by using the rate of decay (dT/dt) of the temperature from $TH_{AM}$ downward (after turning heat from on to off). The rate of decay of the temperature downward with respect to time (dT/dt) from $TH_{AM}$ is also multiplied by the fixed parameter a. Fixed parameter a is a heat transfer coefficient that can be modelled or determined experimentally by exposing the detector body 102 of system 100 to air flow parallel to the bottom surface 112 of the faceplate portion 105 of the detector at a set temperature. Several air velocities are tested and a calibration curve fitted to the experimental data. Fixed parameter a is the output of the known air velocity divided by the known experimental rate of decay for the temperature sensor, (dT/dt), from the active temperature sensor 106. The ratio is relatively constant over a range of air velocities. The experimentally determined ratios are then compared to determine a single value. The comparison can be averaging, filtering or any other statistical processing method. In one embodiment, air velocities used for calibration range from 0 m/s to 10 m/s. These methods of determining the temperature tend to be important in aerospace applications where transient temperatures exist within the housing, and/or when water or dust deposit on the exterior temperature sensor.

Figure 3:
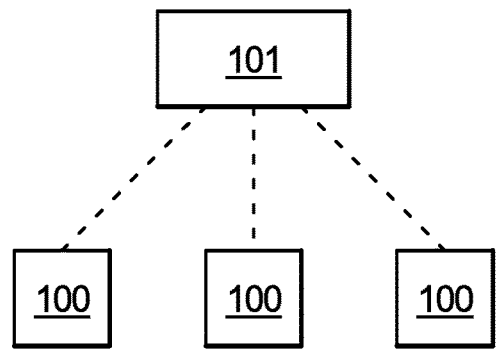
FIG. 3 schematic diagram of an exemplary embodiment of an aircraft management system constructed in accordance with the present disclosure, showing multiple chamberless indoor air quality monitor systems, similar to those of FIG. 1.

As shown schematically in FIG. 3, an aircraft management system 101 includes multiple chamberless indoor air quality monitor systems 100. While only three are depicted in FIG. 3, any number of indoor air quality monitor systems 100 can be used. Aircraft management computer 101 is operatively connected to each of the chamberless indoor air quality monitor systems 100 to correlate and compare data across each of the chamberless indoor air quality monitors 100 to provide an overall assessment of quality for a discrete monitored space, e.g. the cabin, or the aircraft as a whole.

Figure 4:
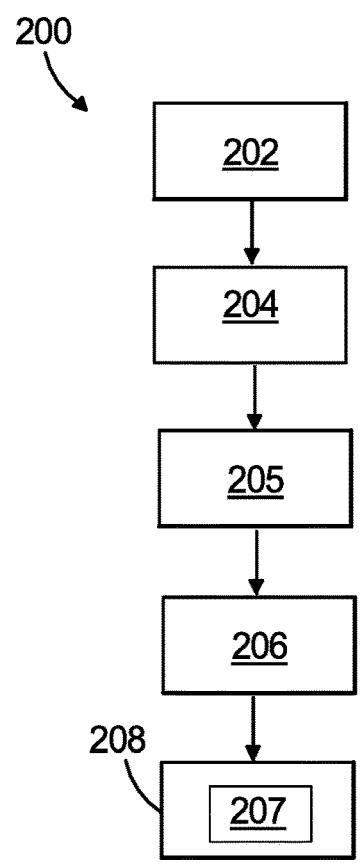
FIG. 4 illustrates a schematic view of a method of operating a chamberless indoor air quality monitor system.

As shown in FIG. 4, a method 200 for measuring temperature in a chamberless indoor air quality monitor system includes, in some embodiments, generating a passive temperature measurement with a passive temperature sensor, e.g. passive temperature sensor 110, as indicated schematically by box 202. Method 200 includes generating active temperature measurements with an active temperature sensor, e.g. active temperature sensor 106, as indicated schematically by box 204. The method includes comparing the active temperature measurements from the active temperature sensor to generate a corrected active temperature measurement ($T_{CA}$) based on a temperature difference ($\Delta T$) over time, as indicated schematically by box 205, and as described above.

With continued reference to FIG. 4, method 200 includes heating the active temperature sensor with a resistive heater, e.g. resistive heater 108, as indicated schematically by box 206. Generating the corrected active temperature measurement based on the temperature difference over time between one or more of the active temperature measurements includes comparing the active temperature measurements before and after heating with the resistive heater. Method 200 includes determining an air velocity across the active temperature sensor, as indicated schematically by box 208, and as described above. Determining the air velocity across the active temperature sensor includes stopping heat to the active temperature sensor and using the rate of decay of the active temperature measurement to determine the air velocity, as indicated schematically by box 207 and as described above with reference to FIG. 6. In some embodiments, comparing active temperature measurements can include using a processor, e.g. processor 114.

The methods and systems of the present disclosure, as described above and shown in the drawings, allow for the use of an indoor air quality monitor system to monitor a variety of conditions such as smoke, temperature, target gases, particulate contaminants, microbial contaminants or other conditions. This eliminates the need for additional, separately powered indoor air quality sensors to be utilized in the same space in which a smoke detector is placed, resulting in substantial consumer and business cost savings. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A chamberless indoor air quality monitor system, comprising:
    a detector body,
    a resistive heater operatively connected to the detector body;
    an active temperature sensor operatively connected to the resistive heater and operatively connected to an outer surface of the detector body configured to take an active temperature measurement; and
    a processor operatively connected to the active temperature sensor configured to receive active temperature measurements from the active temperature sensor and generate a corrected active temperature measurement based on a temperature difference over time between one or more active temperature measurements.

2. The system of claim 1, further comprising a passive temperature sensor operatively connected to a printed circuit board (PCB) and enclosed within the detector body configured to take a passive temperature measurement.

3. The system of claim 1, wherein the active temperature sensor is at least one of a resistance-temperature detector (RTD) or a thermocouple.

4. The system of claim 1, further comprising one or more light sources operatively connected to the detector body configured to emit light into a monitored space.

5. The system of claim 4, further comprising at least three light sensing devices operatively connected to the detector body configured to receive scattered light emitted from the one or more light sources, wherein the at least three light sensing devices share a common centerline axis configured to provide overlapping sensing regions for close proximity detection of the scattered light.

6. The system of claim 5, further comprising a processor configured to evaluate the received scattered light signals for presence of one or more indoor air quality conditions in the monitored space.

7. A chamberless indoor air quality monitor system, comprising:
 a detector body;
 a resistive heater operatively connected to the detector body;
 an active temperature sensor operatively connected to the resistive heater and operatively connected to an outer surface of the detector body configured to take an active temperature measurement;
 one or more light sources operatively connected to the detector body configured to emit light into a monitored space; and
 at least three light sensing devices operatively connected to the detector body configured to receive scattered light emitted from the one or more light sources, wherein the at least three light sensing devices share a common centerline axis configured to provide overlapping sensing regions for close proximity detection of the scattered light.

8. The system of claim 7, further comprising a processor configured to evaluate the received scattered light signals for presence of one or more indoor air quality conditions in the monitored space.

9. The system of claim 7, further comprising a passive temperature sensor operatively connected to a printed circuit board (PCB) and enclosed within the detector body configured to take a passive temperature measurement.

10. The system of claim 7, wherein the active temperature sensor is at least one of a resistance-temperature detector (RTD) or a thermocouple.

11. A method for measuring characteristics near a chamberless indoor air quality monitor system, the method comprising:
 generating a plurality of active temperature measurements with an active temperature sensor operatively connected to an outer surface of the detector body;
 heating the active temperature sensor with a resistive heater operatively connected to the detector body; and
 comparing the active temperature measurements to one another to generate a corrected active temperature measurement based on a temperature difference over time between one or more of the active temperature measurements.

12. The method of claim 11, further comprising generating a passive temperature measurement with a passive temperature sensor operatively connected to a printed circuit board (PCB) and enclosed within a detector body.

13. The method of claim 11, wherein generating the corrected active temperature measurement based on the temperature difference over time between one or more of the active temperature measurements includes comparing the active temperature measurements before and after heating with the resistive heater.

14. The method of claim 11, further comprising determining an air velocity across the active temperature sensor.

15. The method of claim 14, wherein determining the air velocity across the active temperature sensor includes stopping heat to the active temperature sensor and using the rate of decay of the active temperature measurements to determine the air velocity.

16. The method of claim 11, wherein the active temperature sensor is at least one of a resistance-temperature detectors (RTD) or a thermocouple.

17. The method of claim 11, further comprising automatically adjusting the generated corrected active temperature measurement to account for changes in thermal mass of the chamberless indoor air quality monitor system due to a build-up of debris that may become deposited over time on the chamberless indoor air quality monitor system.

18. An aircraft management system comprising:
 chamberless indoor air quality monitor systems; and
 an aircraft management computer operatively connected to each of the chamberless indoor air quality monitor systems to correlate and compare data across each of the chamberless indoor air quality monitor systems, wherein each chamberless indoor air quality monitor system includes:
 a detector body;
 a resistive heater operatively connected to the detector body;
 an active temperature sensor operatively connected to the resistive heater and operatively connected to an outer surface of the detector body configured to take an active temperature measurement; and
 a processor operatively connected to the active temperature sensor configured to receive active temperature measurements from the active temperature sensor and generate a corrected active temperature measurement based on a temperature difference over time between one or more active temperature measurements.

19. The system of claim 18, further comprising a passive temperature sensor operatively connected to a printed circuit board (PCB) and enclosed within the detector body configured to take a passive temperature measurement.

20. The system of claim 18, wherein the active temperature sensor is at least one of a resistance-temperature detector (RTD) or a thermocouple.

21. The system of claim 18, further comprising one or more light sources operatively connected to the detector body configured to emit light into a monitored space.

* * * * *